United States Patent [19]

McHenry

[11] Patent Number: 4,626,528

[45] Date of Patent: Dec. 2, 1986

[54] O,O-DIALKYL O[P-(N-ALKYLCARBAMOYL)PHENYL]-PHOSPHOROTHIONATES AND INSECTICIDAL COMPOSITIONS INCLUDING THE SAME

[75] Inventor: William E. McHenry, Oktibbeha County, Miss.

[73] Assignee: S. C. Johnson & Son, Inc., Racine, Wis.

[21] Appl. No.: 543,715

[22] Filed: Oct. 20, 1983

[51] Int. Cl.$^4$ .......................... A01N 57/14; C07F 9/18
[52] U.S. Cl. ...................................... 514/119; 558/190
[58] Field of Search ........................ 260/943; 424/211; 514/119; 558/190

[56] References Cited

U.S. PATENT DOCUMENTS 3,891,728  6/1975  Drabek et al. ...................... 260/943
4,363,798  12/1982  D'Orzaio ............................ 424/84

FOREIGN PATENT DOCUMENTS 14623  8/1967  Japan ................................... 260/943

OTHER PUBLICATIONS

Journal of Agricultural & Food Chemistry, vol. 30, pp. 1042–1045, Nov.–Dec. 1982, by W. E. McHenry et al, "O,O-Dialkyl".
Journal of Economic Entomology, vol. 73, No. 6, pp. 798–802, 1980, "Laboratory Studies with Nine Amidinohydrazones, A Promising New Class of Bait Toxicants for Control of Red Imported Fire Ants", by D. E. Williams.
Derwent Abstract of Belgium, 655 504.
Kosolapoff, "Organophosphorus Compounds", (1951), pp. 4 & 5.

*Primary Examiner*—Anton H. Sutto

[57] ABSTRACT

Phosphorothionates having the formula

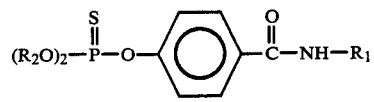

wherein $R_1$ is methyl or ethyl and $R_2$ is an alkyl having from 3 to 6 carbon atoms. These compounds are useful in baits for the control of fire ants and termites.

27 Claims, No Drawings

O,O-DIALKYL O[P-(N-ALKYLCARBAMOYL)PHENYL]PHOSPHOROTHIONATES AND INSECTICIDAL COMPOSITIONS INCLUDING THE SAME

BACKGROUND OF THE INVENTION

This invention relates to a series of O,O-Dialkyl O-[p-(N-Alkylcarbamoyl)phenyl]phosphorothionates and to insecticidal compositions utilizing the same. More particularly, this invention relates to the use of the above class of compounds as control agents for fire ants and termites.

The control of fire ants and termites is especially difficult since these species are organized into highly interrelated colonies. In order to have any effect upon the colonies and to control and/or destroy the same substantial numbers of members in the colony must be killed and for complete eradication of the colony it is necessary to kill the queen. As the queen is far down the colony food chain, a toxicant must not be repellent to the ants or termites when combined with a food attractant, the toxicant must be transferable from colony member to colony member, and the toxicant must kill with delayed toxicity, preferable over as wide a range of concentrations as possible.

Heretofore, the only truly successful toxicant for the control of fire ants and termites has been Mirex, a chlorinated hydrocarbon. This material has been withdrawn from use because of concerns over its toxicity in certain animals and its unusual stability in the environment.

If the toxicant in the bait is too rapid acting, other fire ants and/or termites will develop bait shyness and shy away from the bait.

It has been surprisingly found that certain O,O-dialkyl O-[p-(N-Alkylcarbamoyl)phenyl] Phosphorothionates compounds can be combined with certain conventional bait materials to substantially control and/or eradicate termite and fire ant colonies.

OBJECTS AND ADVANTAGES

It is therefore the primary object of the present invention to provide novel phosphorothionates.

It is a further object of the present invention to provide a novel class of phosphorothionates which are useful in controlling insects, and particularily fire ants and termites.

It is a still further object of the present invention to provide compositions including such novel phosphorothionates for the control of insects, and particularily fire ants and termites.

It is a still further object of the present invention to provide a method for controlling insects, and particularily fire ants and termites using the novel phosphorothionates of the present invention.

Still further objects and advantages of the compounds, compositions and methods of the present invention will become more apparent from the following more detailed description thereof.

DETAILED DESCRIPTION OF THE INVENTION

The compounds of the present invention comprise phosphorothionates having the formula:

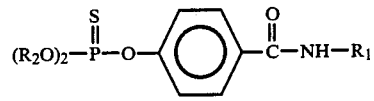

wherein $R_1$ is selected from primary and secondary alkyls having from to 3 to 6 carbon atoms and $R_2$ is selected from methyl or ethyl.

The insecticidal compositions of the present invention comprise from 0.05 to 5% of a compound having the formula:

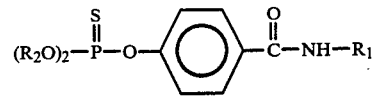

wherein $R_1$ is selected from primary and secondary alkyls having from 3 to 6 carbon atoms and $R_2$ is selected from methyl or ethyl, and an effective amount of an attractant.

The methods of the present invention comprise a method for the control of insects, and particularily fire ants and termites comprising placing a bait comprising an effective amount of an attractant and from 0.05 to 5% of a compound having the formula:

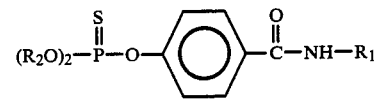

wherein $R_1$ is a primary or secondary alkyl having from 3 to 6 carbon atoms and $R_2$ is selected from methyl or ethyl.

The phosphorothionates of the present invention comprise compounds having the formula:

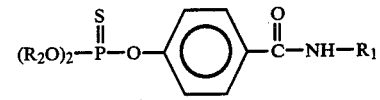

wherein $R_1$ is a primary or secondary alkyl having from 3 to 6 carbon atoms and $R_2$ is methyl or ethyl. It has been surprisingly found that these substituant groups provide good delayed toxicity.

By the term "delayed toxicity" is meant less than 15% mortality of the target insect after one day but more than 85% mortality after 14 days.

Compounds within the above class of compounds include O,O-dimethyl O-[p-(N-isopropyl carbamoyl) phenyl] phosphorothionate, O,O-dimethyl O-[p-(N-isobutyl carbamoyl) phenyl] phosphorothionate, O,O-dimethyl O-[p-(N-isoamyl carbamoyl) phenyl] phosphorothionates, O,O-dimethyl O-[p-(N-secondary butyl carbamoyl) phenyl] phosphorothionate, O,O-dimethyl O-[p-(N-amyl carbamoyl) phenyl] phosphorothionates, O,O-diethyl O-[p-(N-isopropyl carbamoyl) phenyl] phosphorothionates, O,O-diethyl O-[p-(N-isobutyl carbamoyl) phenyl] phosphorothionate, and 0,0-Diethyl O-[p-(N-secondary butyl carbamoyl) phenyl] phosphorothionate. The preferred compounds within the scope of the present invention are O,O-dimethyl O-[p-(N-amyl carbamoyl) phenyl] phosphorothionate and O,O-Diethyl O-[p-(N-isopropyl carbamoyl) phenyl] phosphorothionate.

Generally, these materials are found to have excellent delayed toxicity at concentrations varying from 0.05% to 5% of toxicant in a bait composition. It is preferred to utilize from 0.05 to 2% and most preferably from 0.05 to 0.75% toxicant in the bait.

The compounds of the present invention can be prepared by the following general procedure: A solution composed of phenyl p-hydroxy benzoate and a primary amine are refluxed overnight. The excess amine is then removed from the reaction mixture by conventional means such as distillation at reduced pressure. The remaining oily material is then dissolved in chloroform and washed with hydrochloric acid to remove any residual amine and followed by washing with water to remove the phenol. The solution is then dried. This forms an N-alkyl hydroxy benzamide intermediate. This intermediate is then dissolved in acetone. This mixture is then added to a suspension of sodium hydride in acetone and the resulting mixture is stirred for 15 to 30 minutes in an ice bath. The appropriate dialkyl phosphorothionate is then added dropwise to the mixture. The ice bath is removed and the mixture is stirred at room temperature for 60 to 90 minutes. The reaction mixture is then transferred to a concentrator tube and the solvent is removed by blowing a stream of nitrogen over the sample while heating at 35° C.

The reaction can be represented by the following equations:

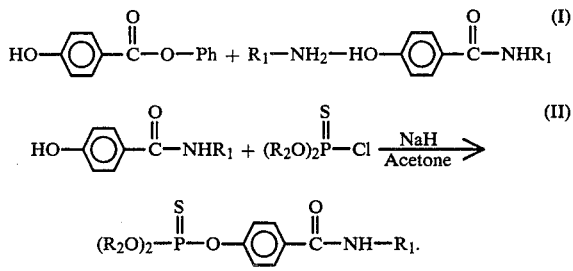

The compounds of the present invention can be mixed with any conventional attractant for insects, and particularily fire ants or termites. Suitable attractants include soybean oil, peanut oil, corn oil, other vegetable oils, sugar, and other food attractants for the fire ants such as peanut butter, honey, etc. and conventional termite attractants such as brown-rot fungus, *lenzites trabea*, impregnated in wood.

The bait compositions can comprise the toxicant of the present invention plus an effective amount of the attractant material and also may, if necessary, include a non-repellent carrier, such as corn cob grits, defatted corn cob grits, degermed corn cob grit, extruded corn pellets, etc. Typically, however, the bait will include 5 to 40 and preferably 10 to 30 percent by weight of the the attractant material and 60 to 95 percent and preferably 70 to 90 percent by weight of a carrier. The bait should be placed in the field in an amount sufficient so that control is achieved. The amount of bait can vary widely depending on the degree of infestation. Typically from 0.5 to 5 pounds of bait should be placed per acre with each pound of bait containing between 0.1 and 10 grams of toxicant compound.

The compounds, composition and methods of the present invention will now be illustrated by way of the following examples which are for the purposes of illustration only and are in no way to be considered as limiting. In the following examples, all parts and percentages are by weight and all temperatures are in degrees centigrade unless otherwise indicated.

EXAMPLE 1

Preparation of N-isopropyl-p-hydroxy benzamide

A solution composed of phenyl para hydroxy benzoate (0.0234 moles) and 15 milliliters of isopropyl amine are refluxed overnight. The excess amine is then removed via distillation at reduced pressure and the remaining oily material is dissolved in 100 milliliters of chloroform and washed first with two 50 milliliters aliquots of 6N hydrochloric acid to remove any residual amine and then with two 50 milliliter aliquots of water to remove the phenol. The solution is dried within sodium sulfate and the volume is reduced to approximately 40 milliliters. The resulting product yielded 85 percent N-isopropyl para hydroxy benezamide having a melting point of 160° to 161° C. This structure was confirmed by NMR.

Preparation of O,O Diethyl O-[P-(n-isopropyl carbamoyl)phenyl] phosphorothionate The suspension of 1.44 grams (0.006 mole) of sodium hydroxide in three milliliters of acetone was treated with 0.003 moles of an isopropyl parahyroxy benzamide prepared above dissolved in three milliliters of acetone. The resulting mixture was stirred for 15 to 30 minutes in an ice bath. Diethyl phosphorothionate (0.03 moles) was added dropwise to the mixture. The ice bath was removed and the mixture was stirred at room temperature for 60 to 90 minutes. The reaction mixture was then transferred to a ten milliliter concentrate tube and the solvent was removed by blowing a stream of nitrogen over the sample while heating at 35° C. The reaction mixture was dissolved in ethyl ether and extracted with three 25 milliliter portions of water followed by extraction with three 25 milliliter portions of 2 percent aqueous sodium carbonate. After drying the solution was filtered and ether was removed by heating at 35° C. and by blowing a stream of dry nitrogen over it. The structure was confirmed by NMR Spectra and had a purity of at least 90 percent.

EXAMPLES 2–8

Using the procedure of Example 1, the following O-Dialkyl O(N-Alkylcarbamoyl)phenyl] phosphorothionates were prepared:

TABLE 1

| Example | Compound | Yield |
|---|---|---|
| 2 | (MeO)$_2$P(S)—O—⟨C$_6$H$_4$⟩—C(O)—NH—CH(Me)—Me | 80% |
| 3 | (MeO)$_2$P(S)—O—⟨C$_6$H$_4$⟩—C(O)—NH—CH$_2$—CH—(Me)$_2$ | 62% |
| 4 | (MeO)$_2$P(S)—O—⟨C$_6$H$_4$⟩—C(O)—NH(CH$_2$)$_2$—CH(Me)$_2$ | 21% |
| 5 | (MeO)$_2$P(S)—O—⟨C$_6$H$_4$⟩—C(O)—NH—CH$_2$—CH—(Me)$_2$ | 39% |

TABLE 1-continued

| Example | Compound | Yield |
|---------|----------|-------|
| 6 | (MeO)$_2$P(=S)−O−C$_6$H$_4$−C(=O)−NH−(CH$_2$)$_4$−Me | 45% |
| 7 | (EtO)$_2$P(=S)−O−C$_6$H$_4$−C(=O)−NH−CH−(Me)$_2$ | 80% |
| 8 | (EtO)$_2$P(=S)−O−C$_6$H$_4$−C(=O)−NH−CH$_2$−CH−(Me)$_2$ | 34% |

Et = Ethyl group
Me = Methyl group

The structure of each of the above compounds was confirmed by NMR Spectra.

EXAMPLE 9

The compositions of Examples 1–8 were screened as bait toxicants for delayed toxicity. The test method was as follows: 30 ml disposable plastic medicine cups were used as test chambers. A 6 mm hole was drilled through the bottom of the cup and a layer of flesh-tone colored dental labstone (Ranson & Randolph Co., Toledo, OH) was poured over the bottom to a thickness of 15 mm. The labstone covered the hole and acted as a wick to absorb water. The cups were placed on a moist foam pad to maintain humidity and prevent desiccation of the ants. Twenty ants were deprived of food for 14 days and placed in each cup 24 hours before the test. The compounds were disolved in soybean oil and offered to the ants using a cotton swab contained in a small vial cup. The treated soybean oil was left in the cup for 24 hours and then replaced with a new cotton swab containing only soybean oil. Mortality counts were made at 1, 2, 3, 6, 8, 20 and 14 days after initial exposure. East test was replicated three times. Each toxicant was tested at 1 percent, 0.5, 0.1 and 0.05 percent concentrations in soy bean oil. The results of this screening are shown in Table 2.

TABLE 2

| | 1% | | 0.5% | | 0.1% | | 0.05% | |
|---|---|---|---|---|---|---|---|---|
| Example | day 1 | day 14 | day 1 | day 14 | day 1 | day 14 | day 1 | day 14 |
| 1 | 65 | 100 | 13 | 100 | 0 | 100 | 0 | 0 |
| 2 | 93 | 100 | 93 | 100 | 22 | 98 | 2 | 93 |
| 3 | 50 | 100 | 0 | 100 | 0 | 100 | 0 | 72 |
| 4 | 2 | 100 | 0 | 98 | 3 | 53 | 3 | 18 |
| 5 | 93 | 100 | 78 | 100 | 7 | 100 | 0 | 77 |
| 6 | 2 | 98 | 2 | 97 | 2 | 87 | 2 | 62 |
| 7 | 0 | 100 | 0 | 100 | 0 | 92 | 0 | 42 |
| 8 | 7 | 77 | 0 | 97 | 0 | 68 | 0 | 77 |

As evidenced by the above table, the compounds of Examples 6 and 7 have exceptional delayed toxicity since they are essentially not toxic at day 1 over a tenfold range of concentration yet have over 85 percent toxicity at day 14 over this same range of concentration, i.e., 0.1 to 1 percent. Similarly, the compounds of Examples 1, 2, 3, and 5 all exhibit very good delayed toxicity having a toxicity at day 14 of over a 10 percent range but yielding minimal toxicity at day 1 over a slightly smaller range. Similarly, the compounds of Examples 4 and 8 also show good delayed toxicity although not as good as the other compounds.

EXAMPLE 10

Laboratory colonies of red imported fire ants were treated with varying amounts of the compound of Example 6 in soy bean oil. The soy bean oil was impregnated on a corn cob grit at a ratio of 15 percent soy bean oil to 85 percent corn cob grit carrier. The concentration of the toxicant is the percentage of toxicant relative to soy bean oil. The ants were allowed access to the bait for 96 hours and then the bait was replaced with a 1:1 ratio of honey and water and their normal diet. About 5 grams of bait were offered to each colony. The results of the mortality in each colony are indicated in Table 3.

TABLE 3

| % concn Soybean oil | mortality, %, in each colony at indicated no. of weeks posttreatment[a] | | | | | | | |
|---|---|---|---|---|---|---|---|---|
| | 1 | 2 | 3 | 4 | 5 | 6 | 7 | 8 |
| 0.5 | 3 | 5 | 8 | 10CN | | | | |
| 0.5 | 7 | 8 | 40 | 40CR | | | | |
| 1.0 | 60 | 85 | 87 | 87 | 87 | 87 | 87 | 87CR |
| 1.0 | 80D | | | | | | | |
| 1.0 | 90 | 94 | 96 | 97 | 97 | 97 | 97 | 97CR |
| 1.0 | 65 | 85 | 92 | 93D | | | | |

[a] D = colony dead; CR = colony appears to be recovering; CN = colony normal.

EXAMPLE 12

The procedure of Example 11 is repeated except that the compound of Example 1 was utilized:

TABLE 3

| % concn Soybean oil | mortality, %, in each colony at indicated no. of weeks posttreatment[a] | | | | | | | |
|---|---|---|---|---|---|---|---|---|
| | 1 | 2 | 3 | 4 | 5 | 6 | 7 | 8 |
| 0.1 | 40 | 45 | 46 | 55 | 55 | 60 | 61 | 62CR |
| 0.1 | 40 | 65 | 66 | 68 | 80 | 81 | 81 | 81CR |
| 0.5 | 65 | 90 | 92 | 98D | | | | |
| 0.5 | 50 | 65 | 65 | 68 | 68 | 69 | 69 | 69CR |
| 1.0 | 40 | 60 | 75 | 95 | 96 | 96 | 96 | 96D |
| 1.0 | 75D | | | | | | | |

[a] D = colony dead; CR = colony appears to be recovering; CN = colony normal.

What I claim is:

1. A method of controlling fire ants and termites comprising placing an effective amount of a bait comprising an effective amount of an attractant and from 0.05 to 5% of a compound having the formula:

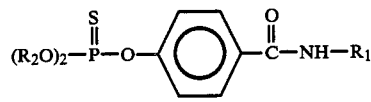

wherein R$_1$ is a primary or secondary alkyl having from 3 to 6 carbon atoms and R$_2$ is selected from methyl or ethyl.

2. The method of claim 1 wherein from 0.5 to 5 pounds of bait are placed per acre, and wherein the bait contains from 0.1 to 10 grams of the compound per pound of bait.

3. The method of claim 1 wherein a carrier comprises from 60 to 95% by weight of the bait.

4. The method of claim 1 wherein R$_2$ is methyl.

5. The method of claim 1 wherein R$_2$ is ethyl.

6. The method of claim 4 wherein R$_1$ is amyl.

7. The method of claim 4 wherein R$_1$ is amyl.

8. The method of claim 5 wherein R$_1$ is isobutyl.

9. The method of claim 1 wherein the bait comprises:

a. from 10–30 percent by weight of an attractant,
b. from 70–90 percent by weight of a carrier, wherein the bait contains from 0.05–2 percent by weight of compound.

10. The method of claim 1 wherein the attractant is selected from the group consisting of soybean oil, peanut oil, corn oil, sugar, peanut butter, honey, wood impregnated with *lenzites trabea* and mixtures.

11. The method of claim 3 wherein the carrier is selected from corn cob grits, defatted corn cob grits, degermed corn cob grits, extruded corn pellets and mixtures thereof.

12. A phosphorothionate having the formula:

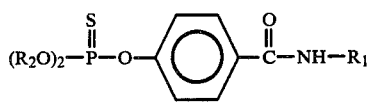

wherein $R_1$ is selected from primary and secondary alkyls having from to 3 to 6 carbon atoms and $R_2$ is selected from methyl or ethyl.

13. The compound of claim 12 wherein $R_2$ is methyl.
14. The compound of claim 12 wherein $R_2$ is ethyl.
15. The compound of claim 13 wherein $R_1$ is amyl.
16. The compound of claim 13 wherein $R_1$ is isopropyl.
17. The compound of claim 14 wherein $R_1$ is isobutyl.
18. An insecticidal bait composition comprising from 0.05 to 5% of a compound having the formula:

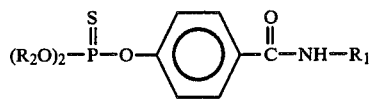

wherein $R_1$ is selected from primary and secondary alkyls having from 3 to 6 carbon atoms and $R_2$ is selected from methyl or ethyl, and an effective amount of an attractant.

19. The bait of claim 18 wherein a carrier comprises from 60 to 95% by weight of the bait.
20. The bait of claim 18 wherein $R_2$ is methyl.
21. The bait of claim 18 wherein $R_2$ is ethyl.
22. The bait of claim 20 wherein $R_1$ is amyl.
23. The bait of claim 20 wherein $R_1$ is isopropyl.
24. The bait of claim 21 wherein $R_1$ is isobutyl.
25. The bait of claim 18 which comprises:
a. from 10–30 percent by weight of an attractant,
b. from 70–90 percent by weight of a carrier, wherein the bait contains from 0.05–2 per cent by weight of compound.

26. The bait of claim 18 wherein the attractant is selected from the group consisting of soybean oil, peanut oil, corn oil, sugar, peanut butter, honey, wood impregnated with *lenzites trabea* and mixtures.

27. The bait of claim 19 wherein the carrier is selected from corn cob grits, defatted corn cob grits, degermed corn cob grits extruded corn pellets and mixtures thereof.

* * * * *